United States Patent [19]

Rizkalla

[11] Patent Number: 5,703,001
[45] Date of Patent: Dec. 30, 1997

[54] PROMOTED SILVER CATALYST

[75] Inventor: Nabil Rizkalla, Riverdale, N.J.

[73] Assignee: Scientific Design Company, Inc., Little Ferry, N.J.

[21] Appl. No.: 738,042

[22] Filed: Oct. 25, 1996

[51] Int. Cl.$^6$ ............................................. B01J 23/50
[52] U.S. Cl. ...................... 502/347; 502/344; 502/348; 502/349; 502/350
[58] Field of Search ........................... 502/344, 347, 502/348, 349, 350

[56] References Cited

U.S. PATENT DOCUMENTS

| | | | |
|---|---|---|---|
| 3,702,259 | 11/1972 | Nielsen | 117/37 R |
| 3,962,136 | 6/1976 | Nielsen et al. | 252/454 |
| 4,007,135 | 2/1977 | Hayden et al. | 252/467 |
| 4,766,105 | 8/1988 | Lauritzen | 502/216 |
| 4,908,343 | 3/1990 | Bhasin | 502/218 |
| 5,051,395 | 9/1991 | Mitchell et al. | 502/348 |
| 5,057,481 | 10/1991 | Bhasin | 502/208 |
| 5,102,848 | 4/1992 | Soo et al. | 502/218 |
| 5,105,053 | 4/1992 | Jacobson et al. | 585/658 |
| 5,418,202 | 5/1995 | Evans et al. | 502/348 |
| 5,504,052 | 4/1996 | Rizkalla | 502/347 |
| 5,597,773 | 1/1997 | Evans et al. | 502/348 |

FOREIGN PATENT DOCUMENTS 0266015  5/1988  European Pat. Off. ......... B01J 23/68

*Primary Examiner*—Helane Myers
*Assistant Examiner*—Alexander G. Ghyka
*Attorney, Agent, or Firm*—William C. Long

[57] ABSTRACT

A rhenium free supported silver catalyst for ethylene oxidation to ethylene oxide is provided containing an alkali metal promoter component and a Group 4b component in which the Group 4b component is added as a compound where the Group 4b compound is the cation.

7 Claims, 2 Drawing Sheets

PROMOTED SILVER CATALYST

BACKGROUND OF THE INVENTION

1. Field of the Invention

The present invention relates to a rhenium-free silver catalyst promoted with alkali metal and a Group 4b component such as zirconium or hafnium for the oxidation of ethylene to ethylene oxide and to the catalyst preparation.

2. Description of the Prior Art

Processes for the production of ethylene oxide involve the vapor phase oxidation of ethylene with molecular oxygen using a solid catalyst comprised of silver on a support such as alumina. There have been extensive efforts by many workers to improve the effectiveness and efficiency of the silver catalyst for producing ethylene oxide. U.S. Pat. No. 5,051,395 provides a comprehensive analysis of such efforts of prior workers.

Among the many prior teachings in this area is that of U.S. Pat. No. 4,007,135 (see also UK 1,491,447) which teaches variously silver catalysts for the production of ethylene and propylene oxides comprised of a promoting amount of copper, gold, magnesium, zinc, cadmium, mercury, strontium, calcium, niobium, tantalum, molybdenum, tungsten, chromium, vanadium, and/or preferably barium, in excess of any present in immobile form in the preformed support as impurities or cements (column 2, lines 1–15), silver catalysts for the production of propylene oxide comprising a promoting amount of at least one promoter selected from lithium, potassium, sodium, rubidium, cesium, copper, gold, magnesium, zinc, cadmium, strontium, calcium, niobium, tantalum, molybdenum, tungsten, chromium, vanadium and barium, in excess of any present in immobile form in the preformed support as impurities or cements (column 2, lines 16–34), as well as silver catalysts for producing ethylene oxide or propylene oxide comprising (a) a promoting amount of sodium, cesium rubidium, and/or potassium, and (b) magnesium, strontium, calcium and/or preferably barium in a promoting amount (column 3, lines 5–8).

U.S. Pat. No. 5,057,481, and related U.S. Pat. No. 4,908,343 are concerned with silver ethylene oxide catalysts which are promoted by various salts, the cation of which is cesium and the anion of which is an oxyanion of an element from Group 3b through 7b of the Periodic Table. U.S. Pat. No. 4,908,343 requires in addition to the cesium salt a salt where the cation is a different alkali metal or an alkaline earth metal and the anion is a halide or an oxyanion of an element having atomic number of 7 or 15 through 83 from the Groups 3a–7a and 3b–7b of the Periodic Table. Zirconate is named among the myriad of oxyanions. U.S. Pat. No. 5,057,481 is similar but requires as promoter a mixture of cesium salts where cesium is the cation and the anion of at least one of the cesium salts is an oxyanion of an element of atomic number 21 to 75 from Groups 3b–7b of the Periodic Table. Zirconate is named among the many oxyanions. U.S. Pat. No. 5,102,848 is also similar but requires as promoter a cation such as cesium and a three component anion comprised of sulfate, fluoride and an oxyanion of an element having atomic number of 21 to 74 from Group 3b to 6b of the Periodic Table.

European Patent Publication 0 266 015 relates to supported silver catalysts promoted with alkali metal and rhenium. A vast number of elements are mentioned as possible rhenium co-promoters including molybdenum, tungsten, chromium, titanium, hafnium, thorium, zirconium, vanadium, thallium, tantalum, niobium, gallium and germanium.

U.S. Pat. No. 5,418,202 is concerned with alleviating the specific instability problems of rhenium promoted silver ethylene oxide catalysts through the use of Group 4b oxo salts such as zirconium oxychloride.

In the context of the bewildering and vast number of references, many of them contradictory, applicant has discovered a novel and improved catalyst for the production of ethylene oxide.

BRIEF DESCRIPTION OF THE INVENTION

The present invention relates to an improved ethylene oxide catalyst which is free of rhenium comprising a porous refractory support having deposited thereon a catalytically effective amount of silver, a promoting amount of alkali metal, optionally a promoting amount of sulfate, and a promoting amount of Group 4b metal applied to the support in the form of a solubilized compound wherein the Group 4b element is cationic.

DETAILED DESCRIPTION

Figure 1:
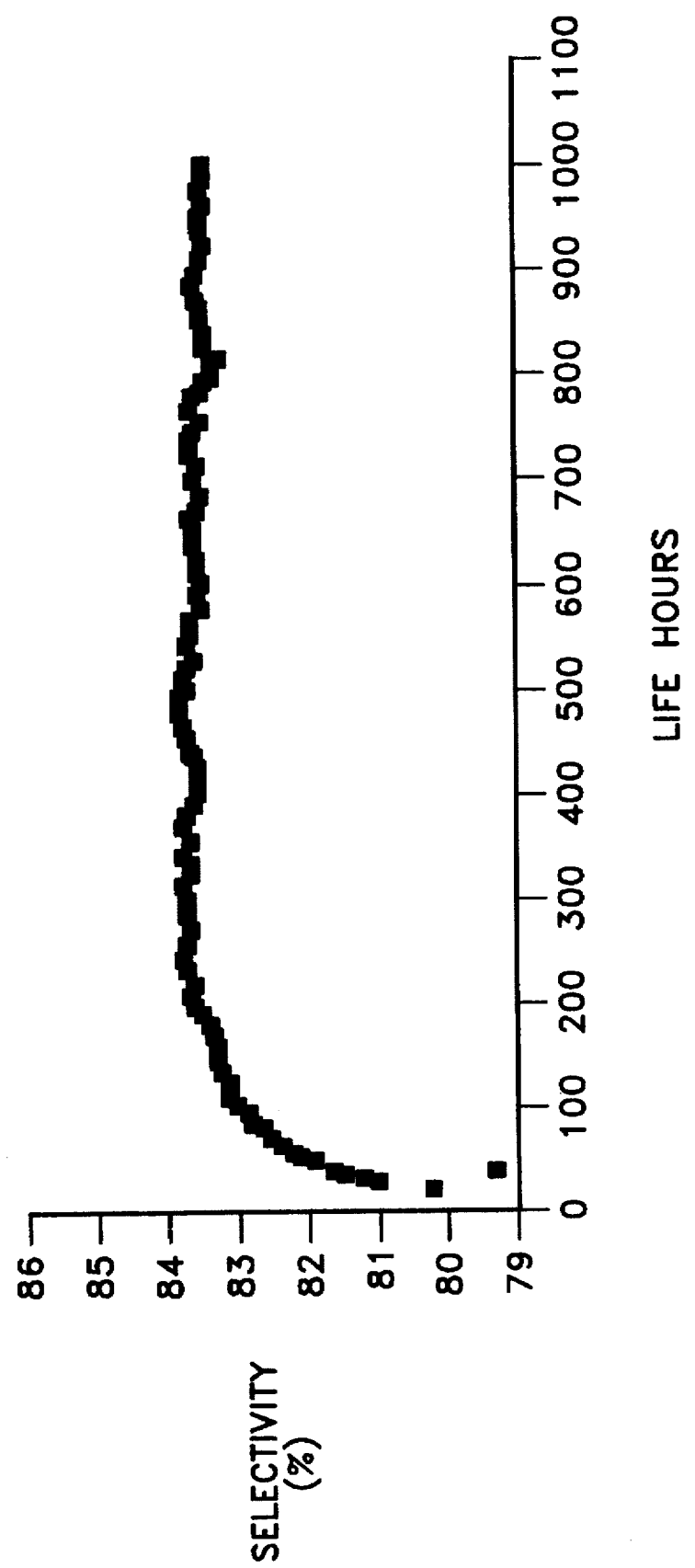
FIGS. 1 and 2 are graphical representations of reaction selectivity as a function of time for catalysts of the invention.

Preferred catalysts prepared in accordance with this invention contain up to about 30% by weight of silver, expressed as metal, deposited upon the surface and throughout the pores of a porous refractory support. Silver contents higher than 20% by weight of total catalyst are effective, but result in catalysts which are unnecessarily expensive. Silver contents, expressed as metal, of about 5–20% based on weight of total catalyst are preferred, while silver contents of 8–15% are especially preferred.

The catalysts of the present invention are free of added rhenium. It has been found that initial selectivity enhancement resulting from rhenium addition is more than offset by the rapid decline in selectivity and activity of such catalysts upon use. The catalysts of this invention are essentially rhenium free.

In addition to silver, the catalyst of the invention also contains an alkali metal promoter selected from potassium, rubidium or cesium, cesium being preferred. The alkali metal promoter amounts and impregnation procedures described in U.S. Pat. No. 3,962,136 are advantageously employed.

Essential to the catalysts of the invention is the provision of a Group 4b promoter component which is applied to the support as a solubilized compound wherein the 4b element is cationic. The Group 4b elements employed are titanium, zirconium and hafnium. Zirconium is preferred expressed as the element, these promoters are incorporated in the catalyst in amount expressed as the element 5–300 ppm by weight based on the weight of the catalyst. Suitable solubilized compounds of Group 4b where the 4b element is cationic are the oxo compounds such as Group 4b oxyhalides, oxynitrates and oxycarbonates as well as Group 4b halides such as Group 4b chlorides and fluorides. Other Group 4b compounds where the Group 4b element is cationic and which are soluble in the impregnation solution include sulfates, nitrates and the like. Specific examples of suitable promoters include the oxychlorides of hafnium, zirconium and titanium, the oxycarbonates and oxynitrates of these same elements, zirconium nitrate, hafnium sulfate, zirconium sulfate, zirconium tetrafluoride, ammonium hexafluorozirconate, and the like.

Preferred also is the provision of sulfur as a promoting catalyst component which component can be added to the catalyst support impregnating solution as sulfate, eg. cesium sulfate, ammonium sulfate, and the like. U.S. Pat. No. 4,766,105 describes the use of sulfur promoting agents, eg. at column 10, lines 53–60, and that disclosure is incorporated herein by reference. The use of sulfur (expressed as the element) in amount of 5–300 ppm by weight based on the weight of catalyst is suitable.

The catalysts of the invention are essentially free of rhenium.

It is preferred that the catalyst also contains a fluorine promoter in amount expressed as the element of 10–300 ppm by weight based on the catalyst. Ammonium fluoride, alkali metal fluoride, as well as fluorides of niobium or tantalum can be used.

Catalysts may be made with supports comprising alumina, silica, silica-alumina or combinations thereof. Preferred supports are those containing principally alpha-alumina, particularly those containing up to about 15 wt % silica. Especially preferred supports have a porosity of about 0.1–1.0 cc/g and preferably about 0.2–0.7 cc/g. Preferred supports also have a relatively low surface area, i.e. about 0.2–2.0 $m^2/g$, preferably 0.4–1.6 $m^2/g$ and most preferably 0.5–1.3 $m^2/g$ as determined by the BET method. See J. A. Chem. Soc, 60, 3098–16 (1938). Porosities are determined by the mercury porosimeter method; see Drake and Ritter, "Ind. Eng. Chem. Anal. Ed.," 17, 787 (1945). Pore and pore diameter distributions are determined from the surface area and apparent porosity measurements.

For use in commercial ethylene oxide production applications, the supports are desirably formed into regularly shaped pellets, spheres, rings, etc. Desirably, the support particles may have "equivalent diameters" in the range from 3–10 mm and preferably in the range of 4–8 mm, which are usually compatible with the internal diameter of the tubes in which the catalyst is placed. "Equivalent diameter" is the diameter of a sphere having the same external surface (i.e. neglecting surface within the pores of the particle) to volume ratio as the support particles being employed.

Preferably, the silver is added to the support by immersion of the support into a silver/amine impregnating solution or by the incipient wetness technique. The silver containing liquid penetrates by absorption, capillary action and/or vacuum into the pores of the support. A single impregnation or a series of impregnations, with or without intermediate drying, may be used, depending in part upon the concentration of the silver salt in the solution. To obtain catalyst having silver contents within the preferred range, suitable impregnating solutions will generally contain from 5–50 wt % silver, expressed as metal. The exact concentrations employed, of course, will depend upon, among other factors, the desired silver content, the nature of the support, the viscosity of the liquid, and solubility of the silver compound.

Impregnation of the selected support is achieved in a conventional manner. The support material is placed in the silver solution until all of the solution is absorbed by the support. Preferably the quantity of the silver solution used to impregnate the porous support is no more than is necessary to fill the pore volume of the porous support.

The impregnating solution, as already indicated, is characterized as a silver/amine solution, preferably such as is fully described in U.S. Pat. No. 3,702,259 the disclosure of which is incorporated herein by reference. One or more of the alkali metal promoters, most preferably cesium, and the impregnation procedures described in U.S. Pat. No. 3,962,136 are advantageously employed.

Known prior procedures of predeposition, co-deposition and postdeposition of various promoters can be employed.

After impregnation, any excess impregnating solution is separated and the support impregnated with silver and the promoter or promoters is calcined or activated. In the most preferred practice of the invention, calcination is carried out as described in commonly assigned U.S. Pat. No. 5,504,052 granted Apr. 2, 1996 and copending application Ser. No. 08/587,281 filed Jan. 16, 1996, the disclosures of which are incorporated herein by reference. The calcination is accomplished by heating the impregnated support, preferably at a gradual rate, to a temperature in the range 300°–500° C. for a time sufficient to convert the contained silver to silver metal and to decompose the organic materials and remove the same as volatiles.

The impregnated support is maintained under an inert atmosphere while it is above 300° C. during the entire procedure. While not wishing to be bound by theory, it is believed that at temperatures of 300° C. and higher oxygen is absorbed in substantial quantities into the bulk of the silver where it has an adverse effect on the catalyst characteristics. Inert atmospheres as employed in the invention are those which are essentially free of oxygen. An alternative method of calcination is to heat the catalyst in a stream of air at a temperature not exceeding 300° C., preferably 270° C.

Catalysts prepared in accordance with the invention have improved performance, especially stability, for use in the production of ethylene oxide by the vapor phase oxidation of ethylene with molecular oxygen. These usually involve reaction temperatures of about 150° C. to 400° C., usually about 200° C. to 300° C., and reaction pressures in the range of from 0.5 to 35 bar. Reactant feed mixtures contain 0.5 to 20% ethylene and 3 to 15% oxygen, with the balance comprising comparatively inert materials including such substances as nitrogen, carbon dioxide, methane, ethane, argon and the like. Only a portion of the ethylene usually is reacted per pass over the catalyst and after separation of the desired ethylene oxide product and the removal of appropriate purge streams and carbon dioxide to prevent uncontrolled build up of inerts and/or by-products, unreacted materials are returned to the oxidation reactor.

The following examples illustrate the invention.

EXAMPLE 1

A silver solution was prepared using the following components (parts are by weight):

Silver oxide—834 parts

Oxalic acid—442 parts

Ethylene Diamine—415 parts

Deionized water—2808 parts

Silver oxide was mixed with water, at room temperature, followed by the gradual addition of the oxalic acid. The mixture was stirred for 15 minutes and at that point the color of the black suspension of silver oxide had changed to the gray/brown color of silver oxalate. The mixture was filtered and the solids were washed with 3 liters of deionized water.

A container which contained the washed solids was placed in an ice bath and stirred while ethylene diamine and water were added slowly in order to maintain the reaction temperature lower than 40° C. After the addition of all the ethylene diamine and water the solution was filtered at room temperature. The clear filtrate was utilized as a silver/amine stock solution for the catalyst preparation.

The support used for the examples was obtained from Norton Company and was made primarily of a-alumina in the form of 5/16 inch cylinders. The support has a surface area of 0.65 m²/g, pore volume of 0.3 cc/g, and medium pore diameter of 1.5μ. About 185 parts of the silver solution was mixed with:

1. 2.86 parts of CsOH solution, (8% Cs in water),
2. 3.6 parts of ammonium hexafluoro zirconate, (2.25% in water), and
3. 1.6 parts of ammonium hydrogen sulphate, (1.25% in water).

The mixture was stirred to assure homogeneity, then added to 400 parts of the support. The wet catalyst was mixed for ten minutes and then calcined.

Calcination, the deposition of silver compound, was induced by heating the catalyst up to the decomposition temperature of the silver salt. This was achieved via heating in a furnace that has several heating zones in a controlled atmosphere. The catalyst was loaded on a moving belt that entered the furnace at ambient temperature. The temperature was gradually increased as the catalyst passed from one zone to the next. It was increased, up to 400° C., as the catalyst passed through seven heating zones. After the heating zones the belt passed through a cooling zone that gradually cooled the catalyst to a temperature lower than 100° C. The total residence time in the furnace was 22 minutes. The atmosphere of the furnace was controlled through the use of the nitrogen flow in the different heating zones.

EXAMPLES 2–9

Using the silver solution and support described above, additional catalysts were prepared.

The catalysts were tested in a tube which was heated by a salt bath. A gas mixture containing 15% ethylene, 7% oxygen, and 78% inert, mainly nitrogen and carbon dioxide, was passed through the catalyst at 300 p.s.i.g., the temperature of the reaction was adjusted in order to obtain ethylene oxide productivity of 160 Kg per hour per m³ of catalyst. The results of the catalyst tests are summarized in the following Table 1. In Examples 1 and 2 the zirconium component was added as dihydrogen hexafluorozirconate, in Example 3 as zirconium tetrafluoride, in Example 4 as zirconium oxide dinitrate and in Example 5 as zirconium oxide dichloride. In Example 6 and 7, hafnium as hafnium oxide dichloride was added. Examples 8 and 9 are comparative, no Group 4B component was used.

TABLE 1

| | Catalyst Promoters | | | | | | |
|---|---|---|---|---|---|---|---|
| Example | Cs ppm | F ppm | S ppm | Zr or Hf ppm | Drying/ Calcination | Sel % | Temp °C. |
| 1 | 585 | 84 | 34 | 70[2] | $N_2$ | 83.5 | 228 |
| 2 | 600 | 84 | 34 | 70[2] | Air | 83.3 | 242 |
| 3 | 585 | 130 | 34 | 70[2] | $N_2$ | 83.5 | 232 |
| 4 | 635 | 125 | 34 | 70[2] | $N_2$ | 83.8 | 237 |
| 5 | 657 | 125 | 34 | 70[2] | $N_2$ | 83.3 | 240 |
| 6 | 623 | 0 | 34 | 195[1] | $N_2$ | 83.0 | 239 |
| 7 | 530 | 75 | 34 | 195[1] | $N_2$ | 83.7 | 236 |
| 8 | 300 | 0 | 0 | 0 | Air | 81.5 | 225 |
| 9 | 600 | 0 | 0 | 0 | $N_2$ | 76.9 | 257 |

[1]Hafnium
[2]Zirconium

Figure 2:
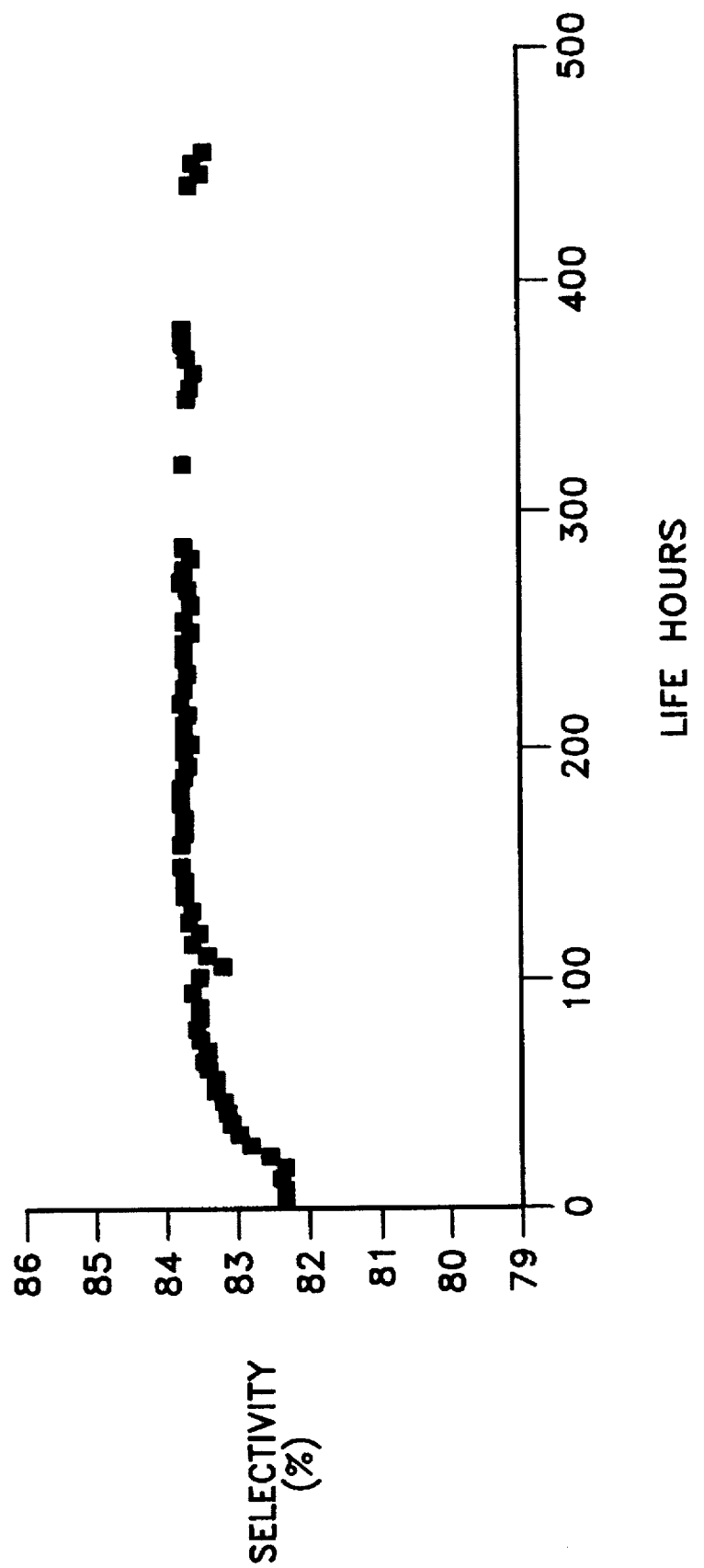

The catalysts of Example 4 and Example 7 above were tested as above indicated for 1000 hours and 450 hours, respectively without a noticeable change in performance. Attached FIG. 1 is a graphic representation of the test results with the catalyst of Example 4 while FIG. 2 is a similar representation of the test results with the catalyst of Example 7. As depicted in these Figures, the catalysts were extremely stable even after extended testing. By contrast, similar catalysts which did not contain the Group 4b evidenced a sharper rate of decline on extended testing.

From the above results in can be seen that:

1. Addition of the Group 4b component to the Ag/Cs catalyst leads to an increase in selectivity, from 81.5–82% up to 83.5–83.8%.

2. Addition of the Group 4b component to the Ag/Cs catalyst leads to an increase in its stability as demonstrated in attached FIGS. 1 and 2 where reaction selectivity was essentially constant after extended testing.

3. Although the presence of the Group 4b component enhances the catalytic activity, especially the catalyst's stability, those catalysts that are calcined in inert atmosphere show superior performance when compared with catalysts of identical formulation and calcined in air.

4. The Group 4b components applied to the support in the form of a solubilized compound wherein the Group 4b element is cationic enhance the catalyst selectivity and stability.

I claim:

1. A rhenium-free catalyst for the oxidation of ethylene to ethylene oxide comprised by weight of 5–30% silver on a solid alumina support having a surface area of 0.2–2.0 m²/g and containing a promoting amount of (1) an alkali metal component and (2) a Group 4b component wherein the Group 4b component is added as a compound having a Group 4b cation.

2. The catalyst of claim 1 wherein the alkali metal component is cesium and the Group 4b component is zirconium.

3. The catalyst of claim 1 wherein the alkali metal component is cesium and the Group 4b component is hafnium.

4. The catalyst of claim 1 wherein the alkali metal component is cesium and the Group 4b component is titanium.

5. The catalyst of claim 1 also containing sulfur as a promoting component.

6. The catalyst of claim 1 also containing fluorine as a promoting component.

7. The process for the preparation of ethylene oxide which comprises reacting ethylene and molecular oxygen in the presence of the catalyst of claim 1.

* * * * *